United States Patent
Takahama et al.

(10) Patent No.: US 7,226,599 B2
(45) Date of Patent: *Jun. 5, 2007

(54) DIAGNOSTIC REAGENT FOR HEPATITIS C VIRUS INFECTION

(75) Inventors: Yoichi Takahama, Hyogo-ken (JP); Junichi Shiraishi, Hyogo-ken (JP)

(73) Assignee: Sysmex Corporation, Hyogo (JP)

(*) Notice: Subject to any disclaimer, the term of this patent is extended or adjusted under 35 U.S.C. 154(b) by 0 days.

This patent is subject to a terminal disclaimer.

(21) Appl. No.: 10/028,172

(22) Filed: Dec. 21, 2001

(65) Prior Publication Data

US 2002/0081630 A1 Jun. 27, 2002

Related U.S. Application Data

(63) Continuation of application No. 08/850,328, filed on May 2, 1997, now Pat. No. 6,379,886.

(30) Foreign Application Priority Data

May 7, 1996 (JP) .............................. 1996-112442

(51) Int. Cl.
*A61K 39/385* (2006.01)
*C12P 21/02* (2006.01)

(52) U.S. Cl. ................ 424/193.1; 424/228.1; 424/189.1; 424/196.1; 424/202.1

(58) Field of Classification Search ............ 424/225.1, 424/184.1, 228.1, 185.1, 196.1, 204.1, 196.11; 435/4, 5, 7.1, 7.92; 436/5.7, 528, 532, 533, 436/535, 820

See application file for complete search history.

(56) References Cited

U.S. PATENT DOCUMENTS

| | | | | |
|---|---|---|---|---|
| 5,106,726 A | * | 4/1992 | Wang ............................ | 435/5 |
| 5,164,299 A | * | 11/1992 | Lambert ...................... | 435/7.92 |
| 5,436,126 A | | 7/1995 | Wang ............................ | 435/5 |
| 5,683,864 A | | 11/1997 | Houghton et al. ............. | 435/5 |
| 5,705,330 A | * | 1/1998 | Shah et al. .................... | 435/5 |
| 5,736,321 A | | 4/1998 | Hosein et al. ................. | 435/5 |
| 5,747,239 A | | 5/1998 | Wang et al. ................... | 435/5 |
| 6,379,886 B1 | | 4/2002 | Takahama et al. ............. | 435/5 |

FOREIGN PATENT DOCUMENTS

| | | |
|---|---|---|
| EP | 0317796 | 10/1988 |
| EP | 0318216 A1 | 5/1989 |
| EP | 0442394 A | 8/1991 |
| EP | 0468527 A | 1/1992 |
| JP | 508219/93 | 11/1993 |
| JP | 06-102273 | 4/1994 |
| JP | 102273/94 | 4/1994 |
| JP | 07-198723 | 8/1994 |
| JP | 198723/95 | 8/1995 |
| JP | 07198723 | 8/1995 |
| WO | WO 90/11089 | 10/1990 |
| WO | WO 91/15771 | 10/1991 |
| WO | WO 93/06247 A1 * | 4/1993 |

OTHER PUBLICATIONS

Lavanchy et al. J. Clinical Laboratory Analysis 1996, vol. 10, pp. 269-276.*
Lee et al. Trnasfusion 1995, vol. 35, pp. 845-849.*
Rosa et al. J. Virol. Methods 1995, vol. 219, pp. 219-232.*
Barrera et al. Vox. Sang. 68:15-18 (1995).
Chien et al. "Diagnosis of Hepatitis C Virus (HCV) Infection Using an Immunodominant Chimeric Polyprotein to Capture Circulating Antibodies:Reevaluation of the Role of HCV in Liver Disease" Proc. Natl. Acad. Sci. USA 89:10011-10015 (1992).
Merrifield. "Solid Phase Peptide Synthesis. I. The Synthesis of a Tetrapeptide" J. Am. Chem. Soc. 85:2149-2154 (1963).
Patent Abstracts of Japan, vol. 095, No. 004, May 31, 1995 and JP 07 020129 A (Tokuama Soda Co. Ltd.) Jan. 24, 1995.
Patent Abstracts of Japan, vol. 095, No. 11, Dec. 26, 1995 and JP 07 198723 A (Nippon Zeon Co. Ltd.) Aug. 1, 1995.
Vyjayanthi et al., Indian Journal of Experimental Biology (1995) 33:329-332.

* cited by examiner

*Primary Examiner*—Bruce R. Campell
*Assistant Examiner*—Bao Qun Li
(74) *Attorney, Agent, or Firm*—Morrison & Foerster LLP

(57) ABSTRACT

A diagnostic reagent for hepatitis C virus infection obtained by sensitizing a solid phase with HCV antigen and a conjugated antigen prepared by chemical bonding of HCV antigen and a carrier protein, and a method of diagnosing hepatitis C virus infection, which comprises adding the diagnostic reagent for hepatitis C virus infection to a sample, and measuring the degree of agglutination of carrier particles as the solid phase. The diagnostic reagent and the method of diagnosis enable many samples to be measured with higher sensitivity and rapidity.

27 Claims, No Drawings

DIAGNOSTIC REAGENT FOR HEPATITIS C VIRUS INFECTION

This application is a continuation application of U.S. application Ser. No., 08/850,328, filed on May 2, 1997, now U.S. Pat. No. 6,379,886B1, which claims foreign priority of Japanese patent application No. 8-112442, filed on May 7, 1996.

BACKGROUND OF THE INVENTION

The present invention relates to a diagnostic reagent for detecting hepatitis C virus (HCV) infection by utilizing immunoagglutination.

In regard to hepatitis C, HCV gene was detected by the research group of Chiron Corporation, U.S.A., in 1988 prior to the detection of HCV. To detect antibodies to HCV, various recombinant antigens or synthetic peptides have been investigated, and kits for detecting HCV-associated antibodies have been developed. The methods of detection now available are agar diffusion, counterimmunoelectrophoresis, radioimmunoassay, enzyme immunoassay, passive hemagglutination, and latex agglutination.

Known HCV antigen proteins for use in the detection of HCV-associated antibodies are core and envelope proteins as structural region proteins, and NS1 to NS5 proteins as non-structural region proteins. One HCV antigen protein alone is not sufficiently high in detection sensitivity, and is also problematical in specificity. Thus, a suitable combination of proteins in structural and non-structural regions is used (Proc. Natl. Acad. Sci. USA 89:10011-10015, 1992). Attempts to increase the detection sensitivity further are also made. With the particle agglutination method, for example, the number of HCV antigens for sensitization of particles is increased, or polypeptide having HCV antigenic activity is heat-treated (Japanese Laid-Open Patent Publication No. 1002273/94); alternatively, a fusion protein constructed from HCV antigen protein and carrier protein is coated onto hydrophilic particles for their sensitization (Japanese Laid-Open Patent Publication No. 198723/95).

The use of synthetic peptide as an antigen has also been attempted, but this use is generally said to lower the detection sensitivity.

Thus, there is a growing demand for a diagnostic reagent and a method of diagnosis which enable many samples to be measured with high sensitivity and rapidity.

SUMMARY OF THE INVENTION

We have conducted intensive studies in an attempt to attain such objectives. As a result, we have found that high sensitivity can be realized by chemically bonding the core antigen, NS3 antigen, NS4 antigen or NS5 antigen of HCV to carrier protein by the glutaraldehyde method to form conjugated antigens, and sensitizing carrier particles with these conjugated antigens. The use of these conjugated antigens has also markedly improved the stability of the particles.

The present invention provides a diagnostic reagent for hepatitis C virus infection obtained by sensitizing a solid phase with HCV antigen and a conjugated antigen prepared by chemical bonding of HCV antigen and a carrier protein.

The carrier protein may be any water-soluble protein, preferably the one with a molecular weight of 10,000 to 1,000,000, more preferably with a molecular weight of 30,000 to 150,000. Preferred examples are bovine serum albumin (BSA), ovalbumin, and hemocyanin. In addition, water-soluble synthetic polymers, such as polyvinyl alcohol and dextran, are also usable.

The solid phase may be carrier particles, a microtiter plate, or a test tube, but carrier particles are preferred. As the carrier particles, known particles generally used in a diagnostic reagent involving the particle agglutination method can be used. Examples include hydrophobic particles such as polystyrene latex, copolymer latex particles having a hydrophilic group such as an amino or carboxyl group on the surface of the particles, erythrocytes, and gelatin particles. More preferable is polystyrene latex.

The HCV antigen protein used in the diagnostics reagent of the present invention is the known structural region protein or non-structural region protein of HCV. The structural region protein may be core protein, while the non-structural region protein may be NS3 protein, NS4 protein or NS5 protein. The amino acid and nucleotide sequences of these antigenic proteins are described in the literature (Officially Published Patent Gazette No. 508219/93). Where the antigenic protein results from does not matter, so long as it has HCV antigenic activity. Natural isolates, chemical synthetics, and genetic recombination products can be used. Of the proteins in these regions, a peptide of varying length can be used as the antigenic protein. Preferably, a peptide composed of 8 or more amino acids containing at least one epitope is used. More preferably, a synthetic peptide having a molecular weight of 1,000 to 5,000 is used. The peptide can be synthesized by a known method in the art, such as solid phase synthesis, fragment condensation, or classical solution synthesis. Preferably, it can be produced by the solid phase peptide synthesis method described in the literature (Merrifield, J. Am. Chem. Soc. 85:2149, 1963).

According to the present invention, one or more of core, NS3, NS4 and NS5 antigen proteins containing one or more different epitopes are combined, and can be used directly, or after conjugation to a carrier protein, to sensitize carrier particles. In the Examples to be described later on, a peptide containing the 49th to 68th amino acids in the core region described in Officially Published Patent Gazette No. 508219/93 is used as the core antigen, a peptide containing the 1706th to 1725th, 1718th to 1737th, and 1724th to 1743rd amino acids in the NS4 region described in Officially Published Patent Gazette No. 508219/93 is used as the NS4 peptide, a peptide containing the 2287th to 2306th, 2299th to 2318th, and 2311th to 2330th amino acids in the NS5 region described in Officially Published Patent Gazette No. 508219/93 is used as the NS5 peptide, and a peptide containing the 1192nd to 1457th amino acids in the NS3 region described in Officially Published Patent Gazette No. 508219/93 is used as the NS3 peptide. However, the antigenic proteins of the present invention are not restricted to these peptides.

Each of the above-described antigenic proteins is chemically bonded to the carrier protein to prepare a conjugated antigen. The antigenic protein has been found to show higher detection sensitivity when sensitizing the carrier particles as a conjugated antigen than when sensitizing them directly. For the antigen protein with a molecular weight of 10,000 or more like the NS3 antigen used in the present invention, however, no marked difference in the sensitivity has been observed. Thus, it is permissible to sensitize the carrier particles directly with such a high molecular weight antigen protein, and sensitize the particles with the other antigen proteins as conjugated antigens. Bonding of the carrier protein and the antigen protein can be performed by a known method using carbodiimide, periodic acid, maleimide or glutaraldehyde. The use of the glutaraldehyde method is preferred, because their bonding by glutaraldehyde-induced crosslinking increases reactivity. For the preparation of the conjugated antigen, the carrier protein and the antigen protein are mixed at a ratio, as the ratio of the numbers of molecules for the two, of about 1:3 to 1:20, preferably about 1:4 to 1:9, more preferably about 1:6 to 1:8. The so prepared conjugated antigen is bound to(or caused to sensitize) carrier particles by a known method, which may be, say, physical adsorption or chemical adsorption. As described previously, the NS3 antigen may be directly caused to sensitize carrier particles without forming a conjugated antigen together with the carrier protein. This can be performed by the same method as described above. Sensitization is carried out in a buffer, a solution with a buffer action, such as phosphate buffer, glycine buffer, TRIS buffer or acetate buffer, preferably at a pH of 3 to 8, more preferably at pH 4 to 5.

The present invention also provides a method of diagnosing hepatitis C virus infection, which comprises adding the aforementioned diagnostic reagent for hepatitis C virus infection to a sample, and measuring the degree of agglutination of the carrier particles by a flow cytometer. The diagnostic reagent for hepatitis C virus infection according to the present invention also reacts with anti-HCV antibodies, if present in the sample, to cause agglutination. The resulting agglutination may be measured visually or by turbidity or absorbance. However, a rapid, high-sensitivity, high-precision/accuracy measurement can be made by optically measuring the agglutinated particles with a full-automatic immunoagglutination measuring system (e.g., PAMIA-30™, TOA MEDICAL ELECTRONICS Co., Ltd) which relies on the principle of a flow cytometer. In detail, the sample is guided into a flow cell, arranged in a row, and passed by a sheath flow mechanism. A laser beam is projected onto it, and the intensity of scattered light produced is measured to tell the degree of agglutination. The number of the agglutinated particles (P: Polymer) and the number of non-agglutinated particles (M: Monomer) are counted. From the P and M, P/T (T=P+M) is calculated, and the presence or absence of anti-HCV antibodies is qualitatively evaluated based on the cutoff value obtained beforehand. This method enables anti-HCV antibodies to be detected with high sensitivity. A suitable particle size of the particles would make measurement possible by a blood analyzer or a particle size analyzer using electrical resistance. However, measurement by an optical method is preferred to avoid a problem such as clogging of the detector.

PREFERRED EMBODIMENTS OF THE INVENTION

The use of the diagnostic reagent for hepatitis C virus infection according to the present invention permits highly sensitive, early diagnosis of infection with hepatitis C virus as compared with commercially available diagnostic reagents. Actually, the diagnostic reagent of the present invention was tested using panel serum composed of several samples taken over time from the same individual in the course of seroconversion of anti-HCV antibodies (e.g., HCV Seroconversion Panel, imported and distributed by Kyowa Medics Co., Ltd, manufactured by BOSTON BIOMEDICA, INC.). The diagnostic reagent for hepatitis C virus infection of the present invention was demonstrated to detect HCV infection in an earlier stage than conventional methods, passive hemagglutination (PHA) using erythrocytes, enzyme immunoassay (EIA) and enzyme-linked immunosorbent assay (ELISA), namely, in the initial stage of infection.

The diagnostic reagent of the present invention was also compared with a diagnostic reagent produced by using the same antigen as in the inventive diagnostic reagent, but directly causing this antigen to sensitize carrier particles without preparing its conjugated antigen together with a carrier protein. The diagnostic reagent of the present invention was found to be superior in the detection sensitivity.

Furthermore, the diagnostic reagent of the present invention does not decrease in the detection sensitivity even after long-term storage. Thus, it proves a stable diagnostic reagent.

The diagnostic method of the present invention, compared with a conventional method such as ELISA, does not involve a complicated washing step, but can be performed by a mere step of mixing the inventive diagnostic reagent for HCV infection (preferably, latex particles sensitized with HCV antigen) with a sample (preferably, a subject's blood). The diagnostic method of the present invention also enables measurement by a measuring system which performs both of the above mixing step and the measuring step full-automatically. Thus, this method is suitable for measuring many samples.

The present invention will be described in greater detail by reference to Examples, which do not limit the scope of the invention.

EXAMPLE 1

Preparation of HCV Conjugated Antigens

For use as HCV antigen, NS3 antigen was produced by genetic recombination based on the description of Example 1 of Officially Published Patent Gazette No. 508219/93. The NS3 antigen was used the 1192nd to 1457th amino acids of HCV protein.

As core antigen, NS4 antigen and NS5 antigen, peptides containing amino acid sequences composed of the 49th to 68th, the 1706th to 1725th, and the 2287th to 2306th amino acids, respectively, described in Officially Published Patent Gazette No. 508219/93 were synthesized by the peptide synthesizer Model 431A (PERKIN ELMER).

Seven volumes of a 0.1% (w/v) solution of core antigen (a peptide of the 49th to 68th amino acids) in 10 mM PBS, pH 7.0, was added to one volume of a 0.1% (w/v) solution of BSA (a commercially available product with a molecular weight of 66,000) in 10 mM PBS, pH 7.0. To the mixture, 10 mM PBS, pH 7.0, was further added to make 9 volumes. Then, a 1% aqueous solution of glutaraldehyde was added to initiate the reaction at a reaction temperature of 30° C. Thirty minutes later, one volume of a 20% aqueous solution of glycine was added to terminate the reaction.

A similar procedure was applied to NS3, NS4 and NS5 antigens as well. That is, 1 to 8 volumes of a 0.1% (w/v) solution of the HCV antigen in 10 mM PBS, pH 6 to 8, was reacted with 1 volume of a 1% (w/v) solution of BSA in 10-mM PBS, pH 6 to 8, to prepare HCV conjugated antigens.

EXAMPLE 2

Production of HCV Antigen-sensitized Latex

To a 5% (w/v) dispersion of polystyrene latex particles (Sekisui Chemical Co., Ltd) with a particle diameter of 0.78 μm in 10 mM PBS, pH 4.0, the NS3 conjugated antigen, the NS4 conjugated antigen and the NS5 conjugated antigen prepared in Example 1 was added in an amount of 50 μg each per ml of the latex dispersion. The mixture was reacted for 24 hours at 4° C. Then, the reaction mixture was centrifuged for 10 min at 12,000 rpm, and 0.1M PBS, pH 7.0, containing 1 mg/ml BSA was added to the same concentration as initially added, to disperse the particles. The dispersion was centrifuged again, and dispersed in the same buffer of the same concentration to produce HCV antigen-sensitized latex.

EXAMPLE 3

Agglutination Reaction

To 10 µl of a sample (a subject's blood), 10 µl of the HCV antigen-sensitized latex (5%) prepared in Example 2 was added, and 80 µl of 0.1M phosphate buffer containing 1 mg/ml BSA was further added. After the mixture was reacted for 15 min at 45° C., the degree of agglutination of the latex particles was measured based on forward-scattered light by means of a full-automatic immunoagglutination measuring system (PAMIA-30™, TOA MEDICAL ELECTRONICS Co., Ltd).

The degree of agglutination is expressed as the percentage of the number of the agglutinated particles to the total number of the particles (P/T, %).

The results of the measurements are presented in Table 1. As shown in Table 1, a sufficient degree of agglutination was obtained with HCV antibody-positive samples, while no agglutination of latex-occurred with HCV antibody-negative samples. Since agglutination was thus observed in samples containing HCV antibodies, one sees that agglutination took place upon the reaction of the HCV antigen-sensitized latex particles with HCV antibodies.

TABLE 1

| Degree of agglutination (P/T, %) | | | | | | | | | |
|---|---|---|---|---|---|---|---|---|---|
| HCV antibody-positive samples | | | | | HCV antibody-negative samples | | | | |
| A | B | C | D | E | F | G | H | I | J |
| 72.52 | 54.56 | 44.89 | 43.02 | 73.00 | 0.95 | 0.90 | 0.82 | 0.82 | 0.92 |

Cutoff value: 2.79%

EXAMPLE 4

Detection Sensitivity at Early Stage

The detection sensitivity for HCV antibody seroconversion was tested using the commercially available HCV Seroconversion Panels PHV901, PHV902 and PHV903 (importer and distributor: Kyowa Medics Co., Ltd, manufacturer: BOSTON BIOMEDICA, INC.) that are composed of several samples taken over time from the same individuals in the course of seroconversion of HCV antibodies. Counting immunoassay (CIA) of the present invention using the diagnostic reagent prepared in Example 2 was compared with the following methods using the products of other companies:

| | |
|---|---|
| Company A: | Passive hemagglutination (PHA) using erythrocytes |
| | HCV antigens used: Core, NS3, NS4 |
| Company B: | Enzyme immununoassay (EIA) |
| | HCV antigens used: Core, NS3, NS4 |
| Company C: | Enzyme-linked immunosorbent assay (ELISA) |

The results obtained are shown in Tables 2, 3 and 4 (the data of Company B's and Company C's products in the tables are the values indicated on the labels attached to the panels). When the diagnostic reagent and the diagnostic method of the present invention were used, HCV infection in Panels PHV902 and PHV903 (the subjects, the presenters of these panels, tested positive for antibodies in PCR from the first day of blood sampling) was detected earlier than the use of the other companies' products.

TABLE 2

HCV Seroconversion Panel PHV901

| | | | Measured value | | Labeled value | | | |
|---|---|---|---|---|---|---|---|---|
| | | | Present invention CIA | Company A PHA | Company B EIA II | | Company C ELISA II | |
| ID | Day of sampling | Number of days | Evaluation | P/T | Evaluation | Evaluation | COI* | Evaluation | COI* |
| PHV901-01 | Sep. 23, 1993 | 0 | − | 1.0 | − | − | 0.2 | − | 0.0 |
| PHV901-02 | Nov. 27, 1993 | 72 | − | 1.1 | − | − | 0.2 | − | 0.0 |
| PHV901-03 | Dec. 29, 1993 | 104 | + | 73.3 | + | + | 1.6 | + | 1.2 |
| PHV901-04 | Dec. 31, 1993 | 106 | + | 74.6 | + | + | 1.7 | + | 1.2 |
| PHV901-05 | Jan. 05, 1994 | 111 | + | 75.3 | + | + | 1.7 | + | 1.4 |
| PHV901-06 | Jan. 07, 1994 | 113 | + | 73.8 | + | + | 1.6 | + | 1.8 |
| PHV901-07 | Feb. 01, 1994 | 138 | + | 73.8 | + | + | 3.8 | + | >4 |
| PHV901-08 | Feb. 09, 1994 | 146 | + | 71.5 | + | + | 3.6 | + | >4 |
| PHV901-09 | Mar. 01, 1993 | 166 | + | 67.0 | + | + | >5 | + | >4 |
| PHV901-10 | Mar. 08, 1994 | 173 | + | 63.9 | + | + | >5 | + | >4 |
| PHV901-11 | Apr. 14, 1994 | 209 | + | 61.7 | + | + | >5 | + | >4 |

Cutoff: 1.75%
COI* = Cutoff index

TABLE 3

HCV Seroconversion Panel PHV902

| | | | Measured value | | | Labeled value | | | | |
|---|---|---|---|---|---|---|---|---|---|---|
| | | | Present invention CIA | | Company A PHA | Company B EIA II | | Company C ELISA II | | |
| ID | Day of sampling | Number of days | Evaluation | P/T | Evaluation | Evaluation | COI* | Evaluation | COI* | PCR |
| PHV902-01 | Feb. 07, 1992 | 0 | – | 1.0 | – | – | 0.2 | – | 0.2 | + |
| PHV902-02 | Feb. 12, 1992 | 2 | – | 1.0 | – | – | 0.2 | – | 0.2 | + |
| PHV902-03 | Feb. 17, 1992 | 7 | + | 3.0 | – | – | 0.4 | – | 0.3 | + |
| PHV902-04 | Feb. 19, 1992 | 9 | + | 4.4 | + | – | 0.8 | – | 0.5 | + |
| PHV902-05 | Feb. 24, 1992 | 14 | + | 17.0 | + | + | 3.9 | + | >4 | + |
| PHV902-06 | Feb. 26, 1992 | 16 | + | 18.0 | + | + | 5.0 | + | >4 | + |
| PHV902-07 | Mar. 02, 1992 | 21 | + | 17.6 | + | + | >5 | + | >4 | + |

Cutoff: 1.75%
COI* = Cutoff index

TABLE 4

HCV Seroconversion Panel PHV903

| | | | Measured value | | | Labeled value | | | | |
|---|---|---|---|---|---|---|---|---|---|---|
| | | | Present invention CIA | | Company A PHA | Company B ETA II | | Company C ELISA II | | |
| ID | Day of sampling | Number of days | Evaluation | P/T | Evaluation | Evaluation | COI* | Evaluation | COI* | PCR |
| PHV903-01 | Feb. 07, 1992 | 0 | – | 0.8 | – | – | 0.2 | – | 0.2 | + |
| PHV903-02 | Feb. 12, 1992 | 5 | + | 2.2 | – | – | 0.4 | – | 0.6 | + |
| PHV903-03 | Feb. 14, 1992 | 7 | + | 4.2 | – | – | 0.5 | – | 0.7 | + |
| PHV903-04 | Feb. 19, 1992 | 12 | + | 12.9 | + | – | 0.8 | + | 1.5 | + |
| PHV903-05 | Feb. 21, 1992 | 14 | + | 11.5 | + | – | 0.7 | + | 1.5 | + |
| PHV903-06 | Feb. 26, 1992 | 19 | + | 28.2 | + | + | 1.7 | + | 4.0 | + |
| PHV903-07 | Feb. 28, 1992 | 21 | + | 29.1 | + | + | 1.9 | + | >4 | + |
| PHV903-08 | Mar. 04, 1992 | 26 | + | 26.6 | + | + | 2.3 | + | >4 | + |

Cutoff: 1.75%

Table 5 Comparison with Diagnostic Reagent Prepared by Direct Sensitization with HCV Antigen The diagnostic reagent of the present invention and a diagnostic reagent prepared by direct sensitization with the same HCV antigen as in the inventive diagnostic reagent were tested for sensitivity for detection of HCV antibodies.

NS3 antigen (obtained by genetic recombination), core antigen (peptide obtained by synthesis), NS4 antigen (peptide obtained by synthesis) and NS5 antigen (peptide obtained by synthesis) were converted into conjugated antigens together with BSA, and used for sensitization in the same manner as in Example 2. Thus, HCV conjugated antigen-sensitized latex was produced.

As a control, HCV antigen-directly-sensitized latex was produced by direct sensitization using the same antigens and the same conditions for sensitization.

Using these latices, the degree of agglutination (P/T, %) of HCV antibody-positive samples (A to E) and that of HCV antibody-negative samples (F to J) were measured by the method of Example 3. Whether each sample was positive or negative for HCV antibodies was evaluated in view of the cutoff value (1.95% for the conjugated antigen-sensitized latex; 1.01% for the antigen-directly-sensitized latex). The results are shown in Table 5.

TABLE 5

| | Conjugated antigen-sensitized latex | | Antigen-directly-sensitized latex | |
|---|---|---|---|---|
| Sample | Degree of agglutination (%) | Evaluation | Degree of agglutination (%) | Evaluation |
| A | 15.87 | Positive | 0.34 | Negative |
| B | 66.28 | Positive | 24.36 | Positive |
| C | 35.28 | Positive | 6.35 | Positive |
| D | 50.98 | Positive | 15.56 | Positive |
| E | 17.88 | Positive | 0.55 | Negative |
| F | 0.46 | Negative | 0.34 | Negative |
| G | 0.56 | Negative | 0.36 | Negative |
| H | 0.79 | Negative | 0.35 | Negative |
| I | 0.62 | Negative | 0.56 | Negative |
| J | 0.65 | Negative | 0.55 | Negative |

In the HCV antibody-positive samples A and E, HCV antibodies were not detected with the diagnostic reagents involving direct sensitization with the antigens, but were detected with the diagnostic reagent of the present invention involving sensitization with the conjugated antigens.

EXAMPLE 6

Test for Long-term Storage Stability

The 5% (w/v) suspensions of HCV antigen-sensitized latices in 0.1 M PBS, pH 7.0, in Example 5 were stored in a refrigerated condition to examine the storage stability of the diagnostic reagents. The results are shown in Table 6.

TABLE 6

|  | HCV antibody-negative pooled serum | | HCV antibody-positive pooled serum | |
| --- | --- | --- | --- | --- |
|  | Conjugated antigen-sensitized | Directly sensitized | Conjugated antigen-sensitized | Directly sensitized |
| 0 month | 0.71% | 0.75% | 41.90% | 12.46% |
| 1 month | 0.71% | 0.72% | 40.85% | 11.56% |
| 3 months | 0.75% | 1.02% | 46.83% | 10.79% |
| 6 months | 0.78% | 1.22% | 43.47% | 10.62% |
| 9 months | 0.82% | 1.50% | 43.86% | 9.79% |
| 12 months | 0.75% | 1.62% | 41.62% | 8.62% |
| 13 months | 0.78% | 1.97% | 43.35% | 8.65% |
| Cutoff value | | | | |
| 0 month | 2.35% | 1.25% | | |
| 1 month | 2.51% | 1.35% | | |
| 3 months | 2.56% | 1.56% | | |
| 6 months | 2.55% | 1.82% | | |
| 9 months | 2.25% | 2.10% | | |
| 12 months | 2.33% | 2.32% | | |
| 13 months | 2.44% | 2.57% | | |

The above results demonstrate that the conjugated antigen-sensitized latex was stable in terms of the degree of agglutination even when stored for a long period of 13 months. In the case of the directly sensitized latex, on the other hand, the test using HCV antibody-negative pooled serum showed gradual increases in the degree of agglutination during long-term storage, while the test using HCV antibody-positive pooled serum showed gradual decreases in the degree of agglutination. Gradual increases in the cutoff value were also observed with the directly sensitized latex.

EXAMPLE 7

Production (2) of HCV Antigen-sensitized Latex

HCV antigen-sensitized latex was prepared by the same procedure as in Example 2 with the use of the same HCV antigens as in Example 1, except that NS3 antigen was not formed into conjugated antigen, but was used for direct sensitization.

EXAMPLE 8

Production (3) of HCV Antigen-sensitized Latex

The same NS3 antigen as in Example 1 was used. Core antigen was a peptide of the 49th to 68th amino acids described in the aforementioned publication (Officially Published Patent Gazette No. 508219/93). NS4 antigen was peptides of the 1706th to 1725th and the 1718th to 1737th amino acids described there. NS5 antigen was peptides of the 2287th to 2306th and the 2299th to 2318th amino acids described there. As in Example 1, 1 to 8 volumes of a 0.1% (w/v) HCV antigen solution was reacted with 1 volume of a 1% (w/v) BSA solution to prepare HCV conjugated antigens. Using them, HCV antigen-sensitized latex was prepared in the same manner as in Example 2.

EXAMPLE 9

Production (4) of HCV Antigen-sensitized Latex

The same NS3 antigen as in Example 1 was used. Core antigen was a peptide of the 49th to 68th amino acids described in the aforementioned publication. NS4 antigen was peptides of the 1706th to 1725th, the 1718th to 1737th and the 1724th to 1743rd amino acids described there. NS5 antigen was peptides of the 2287th to 2306th, the 2299th to 2318th and the 2311th to 2330th amino acids described there. As in Example 1, 1 to 8 volumes of a 0.1% (w/v) HCV antigen solution was reacted with 1 volume of a 1% (w/v) BSA solution to prepare HCV conjugated antigens. Using them, HCV antigen-sensitized latex was prepared in the same manner as in Example 2.

The invention claimed is:

1. A diagnostic reagent for hepatitis C virus (HCV) infection comprising a solid phase sensitized with (a) a genetic recombinant HCV antigen having a molecular weight of 10,000 or more and (b) one or more conjugated HCV antigens, wherein the conjugated HCV antigen comprises a synthetic HCV peptide antigen conjugated with a carrier protein and the synthetic HCV peptide antigen has a molecular weight of less than 10,000.

2. The diagnostic reagent of claim 1, wherein the synthetic HCV peptide antigen of the conjugated HCV antigen is selected from the group consisting of core antigen, NS4 antigen and NS5 antigen.

3. The diagnostic reagent of claim 1, wherein the synthetic HCV peptide antigen of the conjugated HCV antigen is selected from the group consisting of HCV non-structural region proteins and HCV structural region proteins.

4. The diagnostic reagent of claim 1, wherein the synthetic HCV peptide antigens of the conjugated HCV antigens comprise core antigen, NS4 antigen and NS5 antigen.

5. The diagnostic reagent of claim 1, wherein the carrier protein comprises a water-soluble protein.

6. The diagnostic reagent of claim 5, wherein the water-soluble protein is selected from the group consisting of BSA, ovalbumin and hemocyanin.

7. The diagnostic reagent of claim 1, wherein the genetic recombinant HCV antigen is conjugated with a carrier protein.

8. The diagnostic reagent of claim 1, wherein the solid phase comprises carrier particles.

9. The diagnostic reagent of claim 8, wherein the carrier particles are selected from the group consisting of polystyrene latex particle, copolymer latex particle, erythrocyte and gelatin particle.

10. The diagnostic reagent of claim 1, wherein the synthetic HCV peptide antigen has a molecular weight of 1,000 to 5,000.

11. The diagnostic reagent of claim 1, wherein the solid phase comprises a microtiter plate or a test tube.

12. The diagnostic reagent of claim 1, wherein the carrier protein has a molecular weight of 10,000 to 1,000,000.

13. The diagnostic reagent of claim 1, wherein the solid phase is directly sensitized with the genetic recombinant HCV antigen.

14. A diagnostic reagent for hepatitis C virus (HCV) infection comprising a solid phase sensitized with
  (a) a genetic recombinant HCV antigen having a molecular weight of 10,000 or more and
  (b) conjugated HCV antigens comprising
    (i) a first HCV antigen conjugated with a carrier protein; and
    (ii) a second HCV antigen conjugated with a carrier protein;
  wherein the first HCV antigen comprises a first synthetic HCV peptide antigen having a molecular weight of less than 10,000 and the second HCV antigen comprises a second synthetic HCV peptide antigen different from the first synthetic HCV peptide antigen, the second synthetic HCV peptide antigen having a molecular weight of less than 10,000.

15. The diagnostic reagent of claim 14, wherein the genetic recombinant HCV antigen comprises an HCV non-structural region protein.

16. The diagnostic reagent of claim 14, wherein the genetic recombinant HCV antigen comprises NS3 antigen.

17. The diagnostic reagent of claim 14, wherein the first and second HCV antigens are independently selected from the group consisting of HCV non-structural region proteins and HCV structural region proteins.

18. The diagnostic reagent of claim 14, wherein the solid phase is directly sensitized with the genetic recombinant HCV antigen.

19. The diagnostic reagent of claim 14, wherein the solid phase comprises carrier particles.

20. The diagnostic reagent of claim 19, wherein the carrier particle is selected from the group consisting of polystyrene latex particle, copolymer latex particle, erythrocyte and gelatin particle.

21. The diagnostic reagent of claim 14, wherein the first and second synthetic HCV peptide antigens have a molecular weight of 1,000 to 5,000.

22. The diagnostic reagent of claim 14, wherein the solid phase comprises a microtiter plate or a test tube.

23. The diagnostic reagent of claim 14, wherein the carrier protein has a molecular weight of 10,000 to 1,000,000.

24. The diagnostic reagent of claim 14, wherein the genetic recombinant HCV antigen is conjugated with a carrier protein.

25. A diagnostic reagent for hepatitis C virus (HCV) infection comprising a solid phase sensitized with
   (a) a genetic recombinant HCV antigen having a molecular weight of 10,000 or more and
   (b) conjugated HCV antigens comprising
      (i) a first HCV antigen conjugated with a carrier protein; and
      (ii) a second HCV antigen conjugated with a carrier protein;
   wherein each of the first HCV antigen and the second HCV antigen has a molecular weight of less than 10,000, and the first HCV antigen is core antigen.

26. The diagnostic reagent of claim 25, wherein the second HCV antigen is NS4 antigen.

27. The diagnostic reagent of claim 25, wherein the conjugated HCV antigens further comprises a third HCV antigen conjugated with a carrier protein.

* * * * *